(12) United States Patent
Borden (10) Patent No.: US 11,833,268 B2
(45) Date of Patent: *Dec. 5, 2023

(54) IMPLANTABLE BODIES COMPRISING A REGIONAL COMPOSITE

(71) Applicant: Synergy Biomedical, LLC, Wayne, PA (US)

(72) Inventor: Mark D. Borden, Boulder, CO (US)

(73) Assignee: SYNERGY BIOMEDICAL, LLC, Wayne, PA (US)

( * ) Notice: Subject to any disclaimer, the term of this patent is extended or adjusted under 35 U.S.C. 154(b) by 158 days.

This patent is subject to a terminal disclaimer.

(21) Appl. No.: 17/538,124

(22) Filed: Nov. 30, 2021

(65) Prior Publication Data

US 2022/0088267 A1  Mar. 24, 2022

Related U.S. Application Data

(63) Continuation of application No. 16/507,902, filed on Jul. 10, 2019, now Pat. No. 11,191,868.

(51) Int. Cl.
| | |
|---|---|
| *A61L 27/44* | (2006.01) |
| *A61L 27/46* | (2006.01) |
| *A61L 27/50* | (2006.01) |
| *A61L 27/58* | (2006.01) |
| *A61L 31/12* | (2006.01) |
| *A61L 31/14* | (2006.01) |
| *A61L 27/10* | (2006.01) |
| *A61L 27/36* | (2006.01) |
| *A61L 27/12* | (2006.01) |
| *A61L 27/32* | (2006.01) |
| *A61L 27/56* | (2006.01) |

(52) U.S. Cl.
CPC .......... *A61L 27/10* (2013.01); *A61L 27/3608* (2013.01); *A61F 2310/00293* (2013.01); *A61L 27/12* (2013.01); *A61L 27/32* (2013.01); *A61L 27/46* (2013.01); *A61L 27/56* (2013.01); *A61L 27/58* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 8,506,981 B1 | 8/2013 | Borden | |
| 8,871,235 B2 | 10/2014 | Borden | |
| 9,085,665 B1 | 7/2015 | Chang et al. | |
| 2014/0277505 A1* | 9/2014 | Mitchell | A61L 27/10 606/246 |

(Continued)

FOREIGN PATENT DOCUMENTS

EP     1878450 A1    1/2008

OTHER PUBLICATIONS

Hench, et al. "Bonding mechanisms at the interface of ceramic prosthetic materials"; Journal of Biomedical Materials Research 5.6 (1971): 117-141.

(Continued)

*Primary Examiner* — Brian Gulledge
(74) *Attorney, Agent, or Firm* — BAKERHOSTETLER

(57) ABSTRACT

The present patent application is directed to compositions and shaped structures implantable into mammalian bodies, the compositions and shaped structures having localized bioactive surfaces.

36 Claims, 6 Drawing Sheets

Partially Embedded Particles

Fully Embedded Particles

Fully Embedded Particles (with surface removal)

(56) References Cited

U.S. PATENT DOCUMENTS

2017/0112959 A1    4/2017    Erbe et al.

OTHER PUBLICATIONS

Yusong Pan et al: 11 Fabrication and characterisation of functional gradient hydroxyapatite reinforced poly (ether ether ketone) biocomposites, Micro Nano Letters, The Institution of Engineering and Technology, Michael Faraday House, Six Hills Way, Stevenage, Herts. SGI 2AY, UK, vol. 8, No. 7, Jul. 1, 2013 (Jul. 1, 2013), pp. 357-361, XP006046467.
Walsh et al: "Plasma-sprayed titanium coating to polyetheretherketone improves the bone-implant interface", The Spine Journal, vol. 15, No. 5, May 1, 2015 (May 1, 2015), pp. 1041-1049, XP055736790.

* cited by examiner

Fully Embedded bioactive glass spheres on top and bottom surface of a generic cervical spacer implant

Partially Embedded bioactive glass spheres on top and bottom surface of a generic cervical spacer implant Fig. 7A (photograph)　　　Fig. 7B (electron microscope image)

IMPLANTABLE BODIES COMPRISING A REGIONAL COMPOSITE

CROSS REFERENCE TO RELATED APPLICATIONS

The present U.S. Patent Application is a Continuation of U.S. patent application Ser. No. 16/507,902 filed Jul. 10, 2019, the entire disclosure of which is incorporated herein by reference in its entirety.

TECHNICAL FIELD

The present application is directed to biocompatible, implantable compositions having localized biologically active surfaces.

BACKGROUND

Composites incorporate two or more different materials into one composition, e.g., one-shaped structure. Composites are used in musculoskeletal repair and are intended to generally improve the properties of a single material by combining it with one or more other materials that have advantageous properties.

For example, polymer materials are commonly used to create musculoskeletal implants that provide a mechanical function. However, typical polymers do not allow for direct tissue attachment and integration. To address this issue, a musculoskeletal composite can be formed by incorporating a secondary material into the primary, structural polymer form. For example, secondary materials that increase tissue attachment can be added to a structural polymer to improve healing. This type of composite material may be used in musculoskeletal implants where mechanical fixation of the implant to the surrounding bone might improve the implant's function. For example, bone bonding ceramics and bioactive glasses can be added to structural polymers to increase bone attachment.

Bioactive glasses, in particular, are well known to bind directly to bone and have extensive clinical experience as bone graft materials. An exemplary bioactive glass, "45S5 glass," has the following composition: 45% $SiO_2$, 24.5% $Na_2O$, 24.5% CaO, and 6% $P_2O_5$ [Hench, Larry L., et al. "Bonding mechanisms at the interface of ceramic prosthetic materials." *Journal of biomedical materials research* 5.6 (1971): 117-141]. An additional exemplary bioactive glass, "S53P4," is composed of the same oxide components with a different compositional percentage: 53% $SiO_2$, 23% $Na_2O$, 20% CaO, and 4% $P_2O_5$. As bone graft materials, bioactive glasses are known to have bone-bonding properties. When the material is implanted in vivo, bioactive glass forms a hydroxy-carbano-apatite (HCA) layer on the glass surface that allows for direct bone attachment. The formation of this layer is linked to the glass dissolution, subsequent release of calcium (Ca) and phosphorus (P) ions, and the formation of a Ca—P rich layer on the glass surface. The layer eventually crystallizes into hydroxy-carbano-apatite and results in a strong interfacial bond between the bioactive glass and the bone, which improves bone healing around the bioactive glass particles.

In current composite formulations, the ceramic/glass is in a particulate form and is evenly dispersed through the entire structural polymer material. However, this type of dispersion will limit the amount of secondary material in the composite due to strength issues. Although ceramics and glasses can improve tissue attachment, they tend to be brittle materials prone to cracking. When added to a structural material, the brittle ceramic/glass particles weaken the overall strength of the composite. Additionally, the interface between the materials can serve as a point of delamination when stress is applied, due to partial bonding or a lack of bonding between the polymer and the ceramic/glass materials. Further, only the exposed ceramic/glass particles on the surface of the composite provide improved tissue attachment. When evenly dispersed through a polymer material, the interior particles that are fully sequestered from the surface cannot provide the desired tissue-attachment (or "tissue-bonding") properties. These isolated particles only weaken the overall structure of the composite.

In a composite with evenly distributed particles, the combination of materials results in reduction in strength when the composite is formed, relative to the strength of the non-composited, structural material. In an effort to minimize strength loss, composites for structural applications are formed with only a small compositional percentage of the tissue attachment material (i.e., ceramic/glass material), thereby limiting their usefulness in tissue attachment and repair.

In addition to composites, other techniques to improve tissue attachment have been used. These techniques involve adding a tissue attachment coating to a structural material, for example, by plasma spraying tissue attachment materials such as ceramics, glasses, and metals onto a structural polymer. While these processes can partially or entirely coat the surface of structural implant with a material that improves tissue attachment, the coating layers are difficult to bind to the core structural material and can cause the surface layer to delaminate once implanted. When this occurs, the structural integrity of the tissue-implant interface is decreased or eliminated.

Composite materials that result in more substantial tissue attachment, without a significant reduction in composite strength and/or surface integrity, are needed.

SUMMARY

The disclosure is directed to regional composite compositions comprising a core material and a surface material, wherein the surface material is localized to one or more surface regions of the core material, the one or more surface regions comprising about 20% to about 99% by weight of the biologically active material. Shaped structures comprising these composite compositions are also described, as well as methods of making and using these compositions and shaped structures.

DETAILED DESCRIPTION

The disclosure may be more fully appreciated by reference to the following description, including the following definitions and examples. Certain features of the disclosed compositions and methods which are described herein in the context of separate aspects, may also be provided in combination in a single aspect. Alternatively, various features of the disclosed compositions and methods that are, for brevity, described in the context of a single aspect, may also be provided separately or in any subcombination.

Scientific and technical terms used in connection with the present application shall have the meanings that are commonly understood by those of ordinary skill in the art, unless otherwise defined herein.

The compositions of the disclosure are composite compositions, being composed of at least two different materials. These composite compositions include a core material and a surface material. According to the disclosure, the surface material is localized to one or more or all surface regions of the core material. These composite compositions of the disclosure can also be referred to as "regional composites." The composite compositions of the disclosure are distinguishable from composite compositions of the prior art that exhibit substantial material uniformity in the x, y, and z cross-sections of the composite composition. Composite compositions of the disclosure do not exhibit substantial material uniformity (variation of greater than 20%) throughout each region of the x, y, and z cross-sections of the composite compositions. Composite compositions that are not within the scope of the disclosure will exhibit substantial uniformity (with a variation of 20% or less) throughout each region of the x, y, and z cross-sections of those composite compositions. The described compositions can be used as biocompatible, implantable devices in, for example, musculoskeletal repair in mammals. Preferably, the mammal is a human.

The present application describes composite compositions comprising a core material and a surface material wherein the surface material is localized to one or more surface regions of the core material and wherein the surface regions comprise about 20 wt. % to about 99 wt. % of the surface material, based on the weight of the surface region. These composite compositions, when implanted into a mammalian body, provide for improved tissue integration and/or healing, while maintaining strength of the core material. In other aspects, these composite compositions, when implanted into a mammalian body, provide for improved tissue integration, while minimizing strength reduction of the core material.

The composite compositions of the disclosure include a core material. The core material provides a mechanical function to the composite composition, for example, the core material provides strength and/or structure to the composite composition. The composite compositions of the disclosure also include a surface material, localized to one or more surface regions of the core material to form a composite composition of the disclosure. These composite compositions having localized regions of surface material can also be referred to as "regional composites." In these composite compositions, the surface material is localized to one or more or all of the surface regions of the core material. The localization of the surface material to the one or more or all of the core material's surface regions provides for between about 20 wt. % and about 99 wt. % of the surface material present in the composite composition to be in direct contact with surrounding tissue, after implantation of the composite composition into a mammalian subject.

Figure 7A:
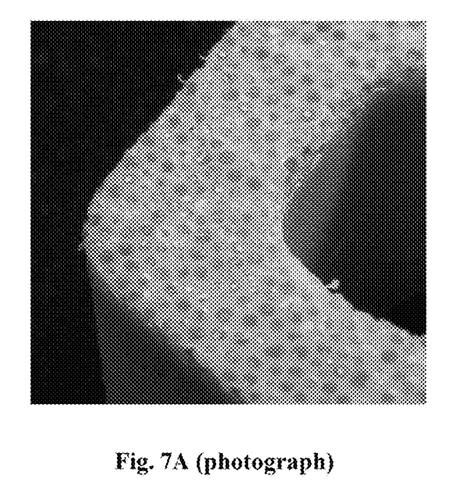
FIG. 7A depicts an embodiment of the disclosure of a regional composite surface comprising a high concentration of embedded glass spheres.
Figure 7B:
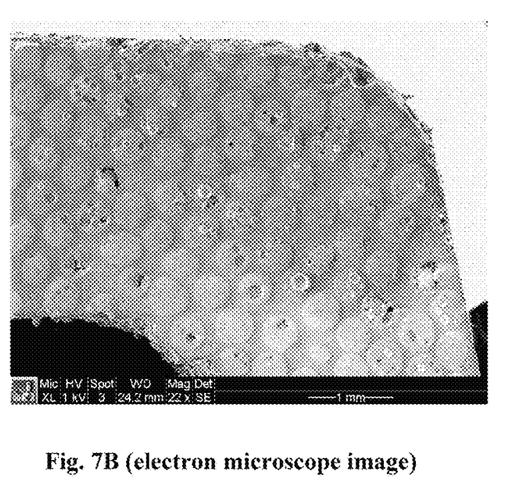
FIG. 7B depicts an embodiment of the disclosure of a regional composite surface comprising a high concentration of embedded glass spheres.

In one aspect, a composite composition as described herein is implanted into a mammalian subject using a tissue attachment material as the surface material. By localizing the tissue attachment material to the one or more surfaces of the core material of the composite composition, the overall mechanical functions of the composite composition are substantially maintained. In some aspects, higher concentrations of the surface material, e.g., tissue attachment material, can be used in the regional composites of the disclosure, as compared to other composites used in the art, since the described surface materials are localized to the outer surface of the composite (see, e.g., FIGS. 7A and 7B). In these aspects, the increase in the amount of surface material, e.g., tissue attachment material, on the surface improves the implant-tissue interface, as compared to other composite materials. Since the increased tissue attachment material is localized to the surface region and is absent from the bulk of the core material, the overall strength of the regional composite is maintained. Unlike other composites in the art, the regional composite allows for both high strength and a high concentration of tissue attachment materials at the implant surface.

In another aspect, a composite composition as described herein is implanted into a mammalian subject using an enhanced healing material as the surface material. These materials may enhance healing through a variety of mechanisms including but limited to cell stimulation, cell differentiation, and cell chemotaxis. In these embodiments, the enhanced healing materials can be used as surface materials on core materials that may already have tissue attachment properties, for example titanium, but lack enhanced healing properties.

The composite compositions of the disclosure include a core material. As used herein, the core material can be any biocompatible, implantable material. In some aspects, the core material is a composite material. In those embodiments wherein the core material is a composite material, the core material comprises a material that provides strength and/or structure, as well as further comprising one or more other materials that provide additional strength and/or structure, but which are non-biologically active. In some aspects, the core material is a composite material that comprises a material that provides strength and/or structure and up to 50 wt. % (e.g., 50, 45, 40, 35, 30, 25, 20, 15, 10, 5, 4, 3, 2, or 1 wt. % or less) of one or more other materials that provide additional strength and/or structure and which are non-biologically active. For example, core materials that are composite materials include core materials that are fiber-reinforced core materials (e.g., glass fiber reinforced materials) or ceramic reinforced core materials.

The core material may be any polymer, metal, or glass material. In some aspects, the core material is non-resorbable polyetheretherketone (PEEK), polyetherketoneketone (PEKK), polyaryletherketone (PAEK), polyurethanes, polyethylene, polypropylene, polyamides, polyarylamides (PARA), polymethylmethacrylate (PMMA), polytetrafluoroethylene, titanium, titanium alloys, stainless steel, tantalum, silicon nitride, or a combination thereof. In other embodiments, the core material is non-resorbable and comprises polyetheretherketone (PEEK), polyetherketoneketone (PEKK), polyaryletherketone (PAEK), polyurethanes, polyethylene, polypropylene, polyamides, polyarylamides (PARA), polymethylmethacrylate (PMMA), polytetrafluoroethylene, titanium, titanium alloys, stainless steel, tantalum, silicon nitride, or a combination thereof.

In other aspects, the core material is a resorbable material and the core material is a poly (hydroxy acid), polyanhydride, polycaprolactone, or a combination thereof. In other embodiments, the core material comprises poly (hydroxy acid), polyanhydride, polycaprolactone, or a combination thereof.

In other aspects, the core material comprises a non-resorbable material and a resorbable material.

In one aspect, the core material is PEEK. In another aspect, the core material comprises PEEK.

In one aspect, the core material is PEKK. In another aspect, the core material comprises PEKK.

In one aspect, the core material is PAEK. In another aspect, the core material comprises PAEK.

In one aspect, the core material is a polyurethane. In another aspect, the core material comprises a polyurethane.

In one aspect, the core material is a polyethylene. In another aspect, the core material comprises a polyethylene.

In one aspect, the core material is a polyamide. In another aspect, the core material comprises a polyamide.

In one aspect, the core material is a polyarylamide. In another aspect, the core material comprises a polyarylamide.

In one aspect, the core material is PMMA. In another aspect, the core material comprises PMMA.

In one aspect, the core material is a polytetrafluoroethylene. In another aspect, the core material comprises a polytetrafluoroethylene.

In one aspect, the core material is titanium. In another aspect, the core material comprises titanium. In one aspect, the core material is a titanium alloy. In another aspect, the core material comprises a titanium alloy.

In one aspect, the core material is stainless steel. In another aspect, the core material comprises stainless steel.

In one aspect, the core material is tantalum. In another aspect, the core material comprises tantalum.

In one aspect, the core material is silicon nitride. In another aspect, the core material comprises silicon nitride.

In one aspect, the core material is a poly (hydroxy acid). In another aspect, the core material comprises a poly (hydroxy acid).

In one aspect, the core material is a polyanhydride. In another aspect, the core material comprises a polyanhydride.

In one aspect, the core material is polycaprolactone. In another aspect, the core material comprises a polycaprolactone.

The compositions of the disclosure further comprise a surface material that is localized to one or more or all surface regions of the core material. As used herein, "surface region" indicates one or more areas at the outer surface of the core material. A surface region can be an entire surface of the core material, or can be limited to a defined area of a surface of the core material. Typically, a surface region will be a defined area (defined length and width, or radius, for example) and a defined thickness where the defined thickness penetrates into the core material. In some embodiments, the surface region has a thickness that penetrates between about 0.25 mm to about 10 mm into the core material, preferably about 0.25 mm to about 5 mm, more preferably about 2 mm. In some aspects, the surface region has a thickness that penetrates between 0.25, 0.5, 0.75, 1, 1.25, 1.5, 1.75, 2, 2.25, 2.5, 2.75, 3, 3.25, 3.5, 3.75, 4, 4.24, 4.5, 4.75, or 5 mm.

In some embodiments, the thickness of the surface material at the surface region has a substantially uniform thickness across the surface region with variations in thickness across the surface being +/−20% or less, e.g., approximately 2 mm +/−20% or less thick across the entire surface region, approximately 0.5 mm +/−20% or less thick across the entire surface region, approximately 5 mm +/−20% or less thick across the entire surface region, or approximately 10 mm +/−20% or less thick across the entire surface region. In some aspects, the variation in thickness across the surface is +/−20, 19, 18, 17, 16, 15, 14, 13, 12, 11, 10, 9, 8, 7, 6, 5, 4, 3, 2, or 1%.

The surface materials of the disclosure are localized to one or more surface regions of the core material. According to the disclosure, "localized" refers to the surface materials being restricted to the one or more surface regions of the core material wherein the non-surface regions of the core material do not comprise surface materials. The x, y, and z cross-sections of the composite compositions of the disclosure will not exhibit substantial material uniformity. Rather, the x, y, and z cross-sections of the composite compositions of the disclosure will include regions having a high concentration of surface material, relative to core material, as well as regions having a low concentration of surface material (or no concentration of surface material), relative to the core material.

In some aspects, the surface material is localized to the surface regions of the core material such that less than 50 wt. % the surface material (for example, 45 wt. %, 40 wt. %, 35 wt. %, 30 wt. %, 25 wt. %, 20 wt. %, 15 wt. %, 10 wt. %, 5 wt. %, 4 wt. %, 3 wt. %, 2 wt. %, or about 1 wt. %) of the composition resides at non-surface regions of the core material. In some aspects, the surface materials of the disclosure are localized such that 50 wt. % or more (for example, 50 wt. %, 55 wt. %, 60 wt. %, 65 wt. %, 70 wt. %, 75 wt. %, 80 wt. %, 85 wt. %, 90 wt. %, 95 wt. %, or at least 99 wt. %) of the surface material resides at the surface region.

Preferably, the surface material of the disclosure is embedded, fully embedded, or partially embedded in the one or more surface regions of the core material and 50 wt. % or more (for example, 50 wt. %, 55 wt. %, 60 wt. %, 65 wt. %, 70 wt. %, 75 wt. %, 80 wt. %, 85 wt. %, 90 wt. %, 95 wt. %, or at least 99 wt. %) of the surface material of the composite composition are embedded, fully embedded, or partially embedded in the one or more surface regions.

Figure 2:
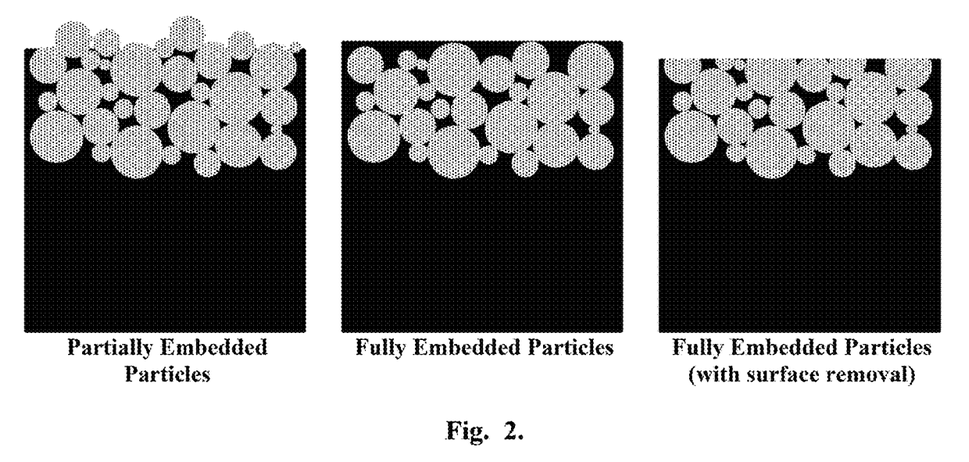
FIG. 2 depicts partially embedded (left-most panel) and fully embedded (middle and right panels) surface material particles in a regional composite according to one embodiment. Composites with partially embedded surface material can have a roughened surface having fully or partially exposed surface material particles. Composites with fully embedded surface material can have a smooth surface comprising minimally exposed surface material particles (middle panel) or highly exposed surface material particles following partial removal of the minimally exposed surface (right panel).

As used herein, the term "embedded" refers to a surface material being disposed in a surface region of the core material. Embedded surface material can be fully embedded, that is, having the entire volume and/or surface area of the surface material fully circumscribed within the volume of the core material, or having the outer surface of the surface material being flush with the surface of the core material (See FIG. 2 and FIG. 3). Embedded surface material can be partially embedded, that is, having a portion of the volume and/or surface area of the surface material extending outward from or breaching the surface of the core material, thereby providing a roughened surface (See FIG. 2 and FIG. 4).

According to the disclosure, the one or more surface regions comprise about 20 wt. % to about 99 wt. % of the surface material, based on the weight of the surface region. For example, the surface regions can comprise 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99 wt. % of the surface material, based on the weight of the surface region. In some aspects, the one or more surface regions comprise about 90 to 99 wt. % of the surface material. In other aspects, the one or more surface regions comprise about 80 to 90 wt. % of the surface material. In other aspects, the one or more surface regions comprise about 70 to 80 wt. % of the surface material. In other aspects, the one or more surface regions comprise about 60 to 70 wt. % of the surface material. In other aspects, the one or more surface regions comprise about 50 to 60 wt. % of the surface material. In other aspects, the one or more surface regions comprise about 40 to 50 wt. % of the surface material. In other aspects, the one or more surface regions comprise about 30 to 40 wt. % of the surface material. In other aspects, the one or more surface regions comprise about 20 to 30 wt. % of the surface material.

The surface materials useful in the compositions of the disclosure can be resorbable or non-resorbable. In some aspects, the surface materials are resorbable. In other aspects, the surface materials are non-resorbable. In some aspects, the surface materials are a combination of one or more resorbable materials and one or more non-resorbable materials, or a combination of resorbable and non-resorbable materials. In those aspects wherein the core material is resorbable and the surface material is or comprises a resorbable material, the resorption rate of the core material and the resorption rate of the surface material will be substantially the same (resorption rates varying less than 30%, for example, varying 25%, 20%, 15%, 10%, 5%, 4%, 3%, 2%, or 1% or less), based on resorption rate analyses that are known in the art.

In other aspects wherein the core material is resorbable and the surface material is or comprises a resorbable material, the resorption rate of the core material and the resorption rate of the surface material will be substantially different (resorption rates varying 30% or more, for example, varying 30%, 35%, 40%, 45%, 50%, 55%, 60%, 65%, 70%, 75%, 80%, 85%, 90%, 95%, 100%, 150%, 200%, 250%, 300%, 350%, 400%, 450%, 500%, 550%, 600%, 650%, 700%, 750%, 800%, 850%, 900%, 950%, 1000% or more), based on resorption rate analyses that are known in the art.

Figure 1:
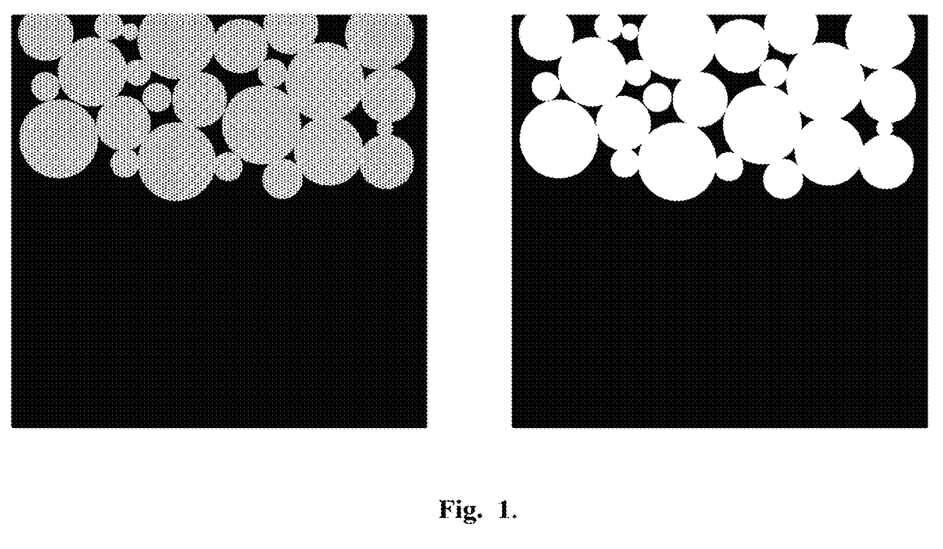
FIG. 1 is a depiction of a cross-section of a regional composite designed to create a porous surface after implantation following regional particle resorption. Left panel: regional composite with spherical surface material prior to or upon implantation. Right panel: regional composite with porous surface following resorption of spherical surface material after implantation.

In those aspects wherein a resorbable surface material is used with a core material that is non-resorbable or resorbable at a slower rate than the surface material, the eventual resorption of the surface material will leave behind a roughened or porous area in the surface region of the core material that promotes tissue in-growth. As tissue grows into the roughened or porous area, an implant-tissue interface develops due to the mechanical interlocking of the implant and the tissue (see FIG. 1). It is understood that the tissue ingrowth properties resulting from the use of a resorbable surface material can be controlled by the shape, size, and concentration of the surface material, and that some configurations of the surface material may be better at promoting tissue in-growth than others.

In some aspects, the surface materials useful in the composite compositions of the disclosure are non-porous materials, for example, biologically active, non-porous glass or ceramic in particle, sphere, or fiber form.

In some aspects, the surface materials useful in the composite compositions of the disclosure are porous materials. In these embodiments, the pores of the porous surface materials are sized such that core material cannot flow into and fill (or partially fill) the pores of the porous surface material. In some embodiments, the pores of the porous surface materials are microporous, e.g., less than 100 microns. For example, the pores of the porous surface materials are 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, or 99 microns in diameter.

In other aspects, the surface materials used in the composite compositions of the disclosure can include a combination of non-porous materials and porous materials.

In those aspects of the disclosure wherein the composite composition includes a porous surface material, the pores of the porous surface material may be substantially non-occluded by core material. In these aspects, a majority of the pores of the porous surface material are not occluded by core material and they are available for interaction with bodily fluids and/or therapeutic agents, as described herein.

In other aspects of the disclosure wherein the composite composition includes a porous surface material, the pores of the porous surface material may be substantially occluded by core material. In these aspects, a majority of the pores of the porous surface material are occluded by core material and are not available for interaction with bodily fluids and/or therapeutic agents.

In those aspects wherein a porous surface material is used in the composite compositions of the disclosure, the composite compositions may further comprise one or more therapeutic agents that have been absorbed and/or adsorbed to the pores of the porous surface material. In some aspects, the one or more therapeutic agents are absorbed into the pores of the porous surface material. In other aspects, the one or more therapeutic agents are adsorbed onto the pores of the porous surface material. Therapeutic agents for use in these embodiments include any agent known to be useful in improving tissue healing, improving tissue attachment, increasing bone bonding, increasing cellular regeneration, or increasing cellular healing. Such agents include, for example, active pharmaceutical ingredients (e.g., antibiotics), proteins, peptides, growth hormones, growth factors, and the like.

In one aspect, a regional composite composition of the disclosure that contains porous surface material is formed using thermal processing or 3-D printing techniques described herein or known in the art. The surface of the composite composition may optionally be further processed to expose more of the porous surface material and porous surface material particles. Once the regional composite composition is formed, a therapeutic agent in a liquid form is applied so as to absorb the therapeutic agent into the microporosity of the surface material. The therapeutic agent can be applied neat or as a composition comprising the therapeutic agent and an excipient or solvent. These therapeutic agent compositions can include solutions, dispersions, emulsions, and the like. After application of the therapeutic agent, the excipient or solvent, if used, can be removed using heat, evaporation, or sublimation. After implantation into a mammal, the therapeutic agent would be released from the microporosity to improve healing.

The surface materials useful in the composite compositions of the disclosure can be of a pre-determined shape and/or size. Surface materials useful in the composite compositions of the disclosure can be, for example, loose particles or granules (in porous or non-porous forms), structures (porous structures or non-porous structures), continuous fibers, segmented fibers, woven fibers, or non-woven fibers.

The particles or granules of the surface materials may have an irregular shape or a uniform shape. In other aspects, the surface material is in the form of a 3-dimensional geometric shape such as, for example, a sphere, spheroid, cylinder, cube, rectangular block, or strut.

Woven fiber surface materials suitable for use in the composite compositions of the disclosure are known in the art and include, for example, meshes, such as titanium meshes, titanium alloy meshes, and stainless steel meshes.

Non-woven fiber surface materials suitable for use in the composite compositions of the disclosure are known in the art can be comprised of, for example, continuous or segmented glass fibers.

Surface materials useful in the composite compositions of the disclosure include bioactive glass, hydroxyapatite (HA), tricalcium phosphate (TCP), biphasic calcium phosphate (HA-TCP), tetracalcium phosphate, brushite, fluorapatite, calcium pyrophosphate, calcium sulfate, titanium, titanium alloys, stainless steel, tantalum, silicon nitride, zirconium, niobium, or a combination thereof.

In some aspects, the surface material is bioactive glass. In other aspects, the surface material comprises bioactive glass. In some aspects, the bioactive glass is bioactive glass spheres such as those described in U.S. Pat. Nos. 8,506,981 and 8,871,235, the entireties of which are incorporated by reference herein.

In preferred aspects, the bioactive glass comprises bioactive glass spheres. Preferably, at least 60-99% of the bioactive glass particles (for example, 60%, 65%, 70%, 75%, 80%, 85%, 90%, 95%, 96%, 97%, 98%, or at least 99%), by weight, will be bioactive glass spheres. More preferably, at least 80-90%, for example 85%, of the bioactive glass particles, by weight, will be bioactive glass spheres.

The bioactive glass spheres used within the scope of the invention include particles that are "substantially spherical." As used herein, "substantially spherical" refers to particles having a substantially circular or oval cross-section and appearing as round to round-ish particles at the microscopic level, for example, in a scanning electron micrograph image. Particles that are oblate spheroids, that is, particles that are rotationally symmetrical ellipsoids with a polar axis shorter than the diameter of the equatorial circle whose plane bisects it, are also within the scope of the "substantially spherical" particles of the invention. Whether the particles are substantially spherical can be determined using methods known in the art. After manufacturing the particles, they are microscopically inspected to qualitatively evaluate whether the particles are substantially spherical. The substantially spherical bioactive glass particles of the invention are shaped in contrast to typical bioactive glass particles having an irregular shape and rough surface that is based on the shattering or grinding of the glass following melt formation. Particles that have a rough surface, are oblong spheres with a tail, are broken spherical fragments, or are particles that are fused together are not considered substantially spherical within the scope of the invention.

In some aspects, the bioactive glass comprises bioactive glass spheres and bioactive glass that is non-spherical. For example, the bioactive glass used in the composite compositions of the disclosure can include 60% by weight of bioactive glass spheres, with the remainder of the bioactive glass being non-spherical. For example, the bioactive glass used in the composite compositions of the disclosure can include 60, 65, 70, 75, 80, 85, 90, 95, 96, 97, 98, 99 or greater than 99% by weight of bioactive glass spheres, with the remainder of the bioactive glass being non-spherical.

In those aspects wherein the surface material is bioactive glass, the glass can be 45S5 glass (e.g., 45% $SiO_2$, 24.5% $Na_2O$, 24.5% CaO, and 6% $P_2O_5$). In those aspects wherein the surface material comprises bioactive glass, the glass can comprise 45S5 glass. In some aspects, the bioactive glass is bioactive glass spheres composed of 45S5 glass. In some aspects, the bioactive glass comprises bioactive glass spheres composed of 45S5 glass.

In those aspects wherein the surface material is bioactive glass, the glass can also be S53P4 glass (e.g., 53% $SiO_2$, 23% $Na_2O$, 20% CaO, and 4% P2O5). In those aspects wherein the surface material comprises bioactive glass, the glass can comprise S53P4 glass. In some aspects, the bioactive glass is bioactive glass spheres composed of S53P4 glass. In some aspects, the bioactive glass comprises bioactive glass spheres composed of S53P4 glass.

The bioactive glass particles (whether spheres or non-spheres) of the invention preferably incorporate a unimodal or bimodal particle size distribution. Particle size and particle size distribution can be measured using methods known in the art, including laser diffraction particle size analysis. As used herein, "bimodal particle size distribution" refers to the materials of the invention wherein the majority of the particle sizes fall within the scope of two particle size distributions. A preferred embodiment of a bimodal distribution of the invention will comprise a minority of small particles and a majority of larger particles. Compositions of the invention comprising a bimodal particle size distribution may include a minority of particle sizes falling outside the scope of either of the two specified particle size distributions. Preferably, at least 60-99% of the particles, by weight, will fall within the two specified particle size distributions. More preferably, at least 80-90%, for example 85%, of the particles, by weight, will fall within the two specified particle size distributions.

Multimodal particle size distributions are also envisioned. In such multimodal distributions, a majority of the particles sizes falls within the scope of three or more particle size distributions.

In preferred embodiments, the materials of the invention will include bioactive glass particles having a first particle size distribution between 32 and 200 μm and a second particle size distribution of between 300 and 800 µm. Preferably, between 5% and 50% of the particles, more preferably about 10% of the particles, by weight, will have particle sizes falling within the 32 to 200 µm, more preferably within a 90 to 180 µm range.

Also preferred are embodiments having between 50% and 95% of the particles, more preferably about 90% of the particles, by weight, particles sizes falling within the 300 and 800 µm range, preferably 355 to 500 µm.

In particularly preferred embodiments, the materials of the invention will include bioactive glass particles having a first particle size distribution between 90 and 180 µm and a second particle size distribution of between 355 and 500 µm.

In some aspects, the surface material is HA. In other aspects, the surface material comprises HA.

In some aspects, the surface material is TCP. In other aspects, the surface material comprises TCP.

In some aspects, the surface material is HA-TCP. In other aspects, the surface material comprises HA-TCP.

In some aspects, the surface material is tetracalcium phosphate. In other aspects, the surface material comprises tetracalcium phosphate.

In some aspects, the surface material is brushite. In some aspects, the surface material comprises brushite.

In some aspects, the surface material is fluorapatite. In some aspects, the surface material comprises fluorapatite.

In some aspects, the surface material is calcium pyrophosphate. In some aspects, the surface material comprises calcium pyrophosphate.

In some aspects, the surface material is calcium sulfate. In some aspects, the surface material comprises calcium sulfate.

In some aspects, the surface material is titanium. In some aspects, the surface material comprises titanium.

In some aspects, the surface material is a titanium alloy. In some aspects, the surface material comprises titanium alloy.

In some aspects, the surface material is stainless steel. In some aspects, the surface material comprises stainless steel.

In some aspects, the surface material is tantalum. In some aspects, the surface material comprises tantalum.

In some aspects, the surface material is silicon nitride. In some aspects, the surface material comprises silicon nitride.

In some aspects, the surface material is zirconium. In some aspects, the surface material comprises zirconium.

In some aspects, the surface material is niobium. In some aspects, the surface material comprises niobium.

The composite compositions of the disclosure may be formed into shaped structures useful for implantation into a mammalian body, using methods known in the art. For example, the shaped structures of the disclosure can be prepared by heating a core material to a semi-molten state and pressing a surface material into one or more surface regions of the semi-molten core material using mechanical means. In other aspects, the shaped structures of the disclosure can be prepared by melting a core material and pouring the melted core material over a layer, of predetermined thickness, of a surface material.

In other aspects, the shaped structures of the disclosure can be prepared by compression molding at least one layer of a surface material on one or more surface regions of a layer of a core material.

In some aspects, the shaped structures of the disclosure can be prepared by a process comprising forming the surface material into a pre-determined shape. For example, particles of a surface material can be loaded into a mold and then sintered and cooled to form a pre-determined shape, having a pre-determined thickness. In some aspects, these shaped surface materials will comprise macroporosity. For example, the shaped surface materials will comprise pores that are greater than 100 microns, for example, 110, 115, 125, 150, 175, 200, 225, 250, 275, 300, 325, 350, 375, 400, 425, 450, 475, or 500 microns. Preferred macroporosities will include pores greater than 100 microns to about 400 microns.

The processes for forming the described shaped structures of the disclosure using shaped surface materials can further comprise melting a core material and pouring the melted core material over the shaped surface material. In other aspects, the processes for forming the described shaped structures of the disclosure using shaped surface materials can further comprise compression molding a molten or semi molten core material into the shaped surface material or compression molding the shaped structure onto one or more surface regions of a molten or semi-molten core material.

In other aspects, the shaped structures of the disclosure can be prepared by melt processing a composite layer of the surface and core material, machining the melt-processed layer of surface and core material into a pre-determined shape, and sintering or melting the machined shaped surface material on one or more surface regions of the core material.

In other aspects, the shaped structures of the disclosure can be prepared using 3-D printing methods or laser sintering methods. In such aspects, a layer of a surface and core material is 3-D printed or laser sintered, and a layer of core material is 3-D printed or laser sintered onto the surface-core material composite layer, followed by another layer of surface and core material. In other such aspects, a layer of a core material is 3-D printed or laser sintered, and a layer of surface and core material is 3-D printed or laser sintered onto the core material layer. These processes can be repeated as many times as necessary to produce the pre-selected shaped structure.

Any method of making the shaped structure of the disclosure, either known in the art or described herein, can be used alone or in combination with other known or described methods.

In some aspects, the methods of making a shaped structure of the disclosure comprises a partial surface removal step. In particular, in fully embedded surface material compositions, additional surface material can be exposed by partial removal of the regional composite layer. In some aspects, the surface removal step comprises machining the shaped structure. In other aspects, the surface removal step comprises particle blasting (e.g., bead blasting) the shaped structure. In other aspects, the surface removal step comprises sanding the shaped structure. In some aspects, the surface removal step comprises machining the shaped structure and sanding the shaped structure. In some aspects, the surface removal step comprises machining the shaped structure and particle blasting the shaped structure. In some aspects, the surface removal step comprises particle blasting the shaped structure and sanding the shaped structure.

In some aspects, the shaped structure of the disclosure is in the form of a surgical implant. In some aspects, the shaped structure of the disclosure is in the form of an interbody spacer. In some aspects, the shaped structure of the disclosure is in the form of a suture anchor. In some aspects, the shaped structure of the disclosure is in the form of a surgical screw. In some aspects, the shaped structure of the disclosure is in the form of a surgical plate. In some aspects, the shaped structure of the disclosure is in the form of an anterior cruciate ligament (ACL) interference screw. In some aspects, the shaped structure is in the form of a surgical trauma plate. In some aspects, the shaped structure is in the form of a surgical trauma pin. In some aspects, the shaped structure is in the form of a craniomaxillofacial plate. In some aspects, the shaped structure is in the form of a craniomaxillofacial implant.

The following examples are to be illustrative, only, and are not intended to limit the invention.

EXAMPLES

The compositions of the disclosure can be created using any single processing technique or combination of processing techniques understood by those skilled in the art.

Example 1

Composite compositions for use as, for example, spinal interbody fusion implants (cervical fusion implants) were prepared using PEEK and bioactive glass spheres. A compression molding process was used to create a regional composite block with bioactive glass spheres/PEEK regions on the top and bottom surfaces of the block.

The compression molding process generated two types of surfaces. A first compression molding process, produced a surface with fully embedded spheres. A second compression molding process, using a greater amount of bioactive glass spheres than that used in the first compression molding process, produced a surface with partially embedded spheres. Blocks were machined into general cervical interbody spacers using methods of machining known in the art.

PEEK raw material was machined into blocks that fit inside a 20×50 mm stainless compression mold that had been partially pre-filled with bioactive glass spheres. The mold was tapped to create an even layer of bioactive glass spheres that was 1-3 mm deep (depth dependent on amount of bioactive glass spheres used). The PEEK block was then placed in the mold and lightly pressed into contact with the bottom bioactive glass sphere layer. Another layer of bioactive glass spheres was added to the top of the PEEK block within the mold. The mold was tapped again to create an even upper layer. The top piece of the mold was inserted into the mold well. The final mold configuration consisted of a layer of bioactive glass on the top and bottom of the PEEK block. The mold was placed in a kiln at 750° F. for 1 hour. The mold was removed from the kiln and compressed with 250 lbs. of force for 2 minutes. The mold was then allowed to cool with a constant 20 lbs. of pressure until fully cooled. The mold was dissembled and the composite block was removed. The block was then machined into the general shape of a cervical interbody fusion device using standard methods.

Figure 3:
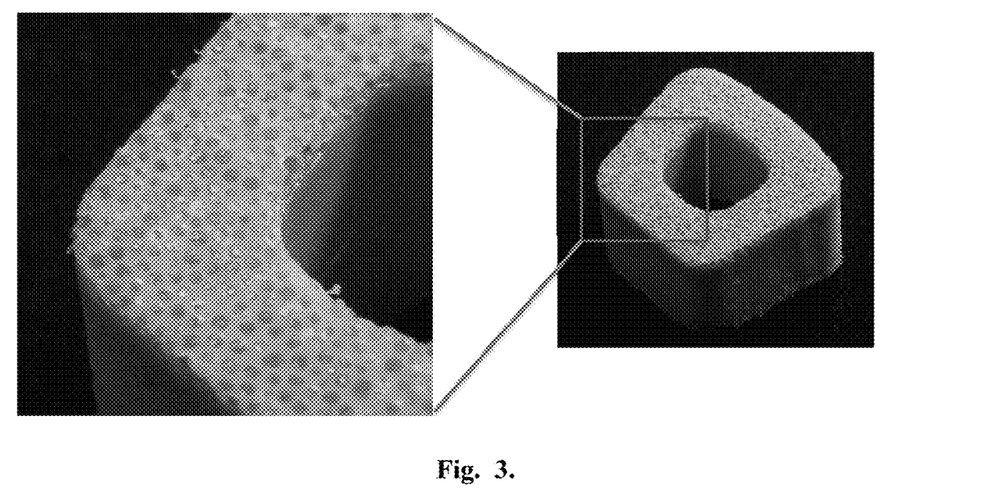
FIG. 3 depicts an embodiment of the disclosure of a shaped body comprising a regional composite composition with fully embedded bioactive glass spheres with partial removal of the surface.
Figure 4:
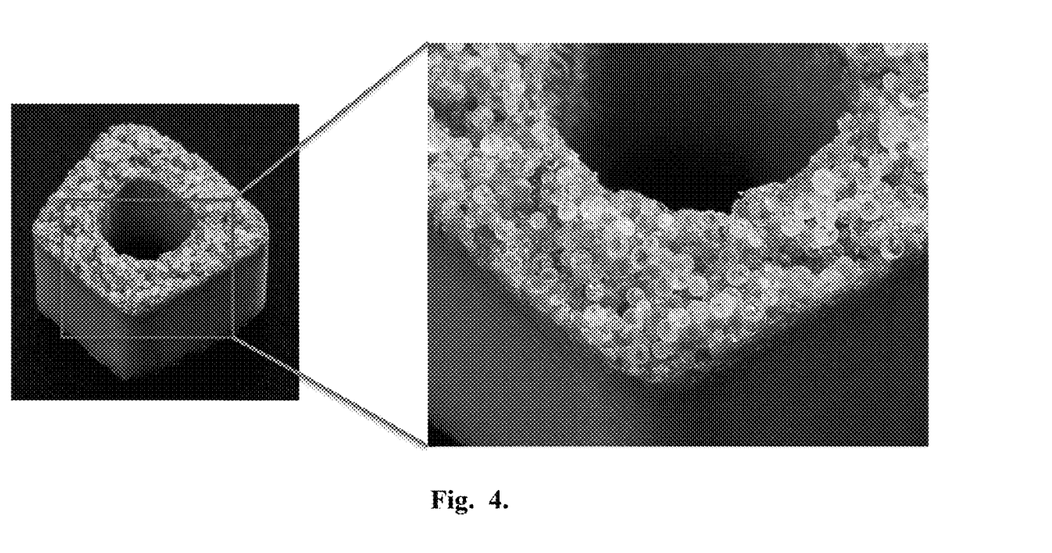
FIG. 4 depicts an embodiment of the disclosure of a shaped body comprising a regional composite composition with partially embedded bioactive glass spheres.

As seen in FIGS. 3 and 4, two distinct surfaces were created. The surface creation was controlled by the amount of the surface material (i.e., bioactive glass spheres) used in the mold. The fully embedded sphere surface in FIG. 3 was created with created with a 1 g bioactive glass sphere layer. The partially embedded sphere surface in FIG. 4 was created with a 2 g bioactive glass sphere layer.

In this process, the PEEK was heated to a temperature sufficient to allow the PEEK to flow around the spheres to a certain depth. The combination of heating temperature, heating time, compression force, compression time, and surface particle amount spacing dictated the amount of flow around the bioactive glass spheres. With a smaller amount of bioactive glass in the top and bottom layer (1 g), the PEEK flowed completely around all surface particles and resulted in a fully embedded surface. Following molding, surface spheres were further exposed with light surface sanding of the composite (see FIG. 3).

When a larger amount of spheres was used (2 g) with the same compression molding parameters (heating temperature, heating time, compression force, compression time), the PEEK flow could not penetrate through the entire sphere layer. This fully embedded the spheres in contact with the PEEK block. However, since the depth of the sphere layer was greater than the PEEK flow distance, this resulted in partial embedding of the uppermost spheres. This resulted in a roughened surface with both fully and partially embedded spheres (see FIG. 4).

To further characterize the implants, microCT imaging was used. MicroCT imaging is able to differentiate between radiopaque and radiolucent materials. Since the PEEK material was radiolucent and the bioactive glass spheres were radiopaque, the microCT scans could clearly identify the layer of bioactive glass embedded within the PEEK core material.

Figure 5:
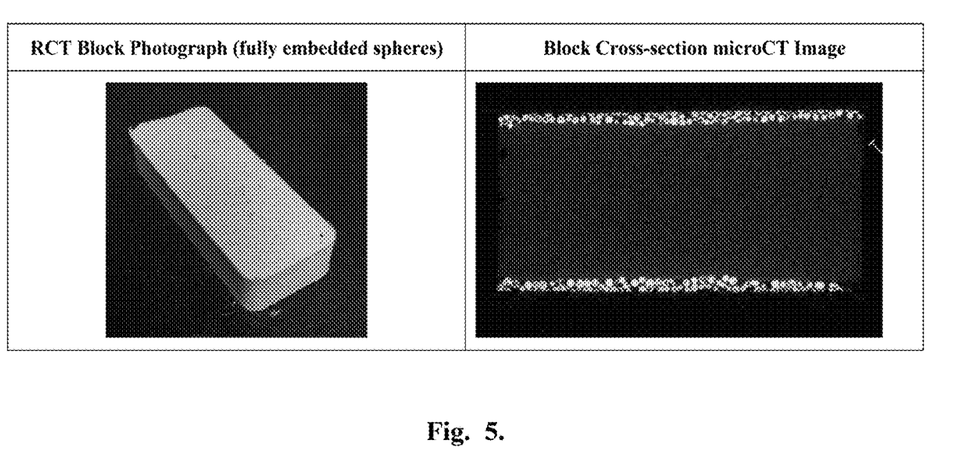
FIG. 5 depicts an embodiment of the disclosure of a shaped body comprising a regional composite composition with fully embedded bioactive glass spheres, as well as a cross-sectional microCT image of the shaped body.

MicroCT imaging provided cross-sectional and 3-D images of the regional composite composition block. An image of a composite composition block with a fully embedded surface is shown in FIG. 5. The cross-sectional microCT image shows a layer of embedded spheres at the top and bottom of the block. The layer is relatively uniform and spherical particle shapes can be seen. As seen by the image, a regional composite was formed on the top and bottom of the block. The spheres (surface material) are completely localized to the outer surface region of the block with a central PEEK area (core material) that does not contain bioactive glass spheres.

Figure 6A:
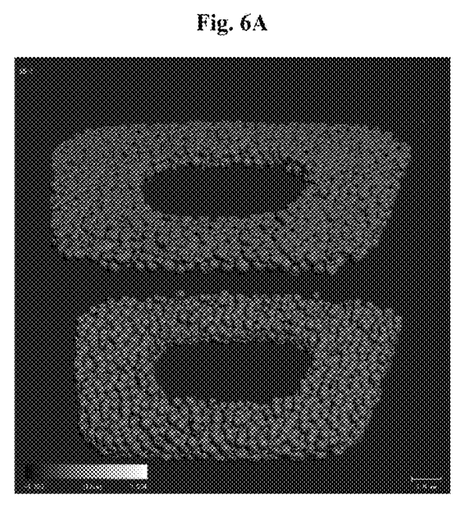
FIG. 6A depicts a microCT image of a shaped body comprising a regional composite composition of the disclosure with fully embedded surface spheres.
Figure 6B:
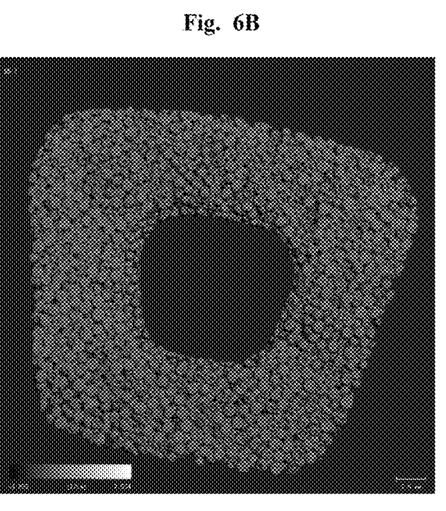
FIG. 6B depicts a microCT image of a shaped body comprising a regional composite composition of the disclosure with fully embedded surface spheres.
Figure 6C:
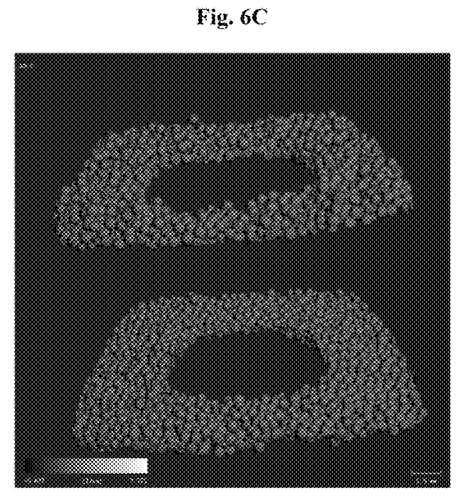
FIG. 6C depicts a microCT image of a shaped body comprising a regional composite composition of the disclosure with partially embedded surface spheres.
Figure 6D:
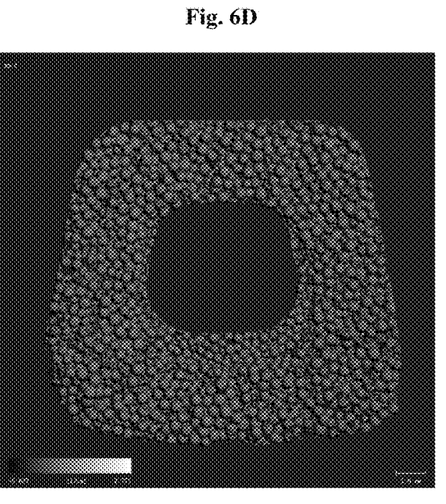
FIG. 6D depicts a microCT image of a shaped body comprising a regional composite composition of the disclosure with partially embedded surface spheres.

MicroCT imaging was also conducted on the cervical spacer implants made with a fully embedded particle surface and a partially embedded particle surface. This is shown in FIGS. 6A-6D. These 3-D images show the creation of a regional composite and the differences in surface topography between the two surface types. Both implants have a relatively uniform region of the bioactive glass spheres localized to the top and bottom of the implant that is substantially similar in thickness. The implants were differentiated by the smooth surface of the fully embedded spheres compared (FIGS. 6A and 6B) to the rough surface resulting from the partially embedded spheres (FIGS. 6C and 6D). Overall, the images showed successful creation of a regional composite and flexibility in controlling the surface topography. The ability to tailor the surface roughness is advantageous in when designing an implant for specific musculoskeletal applications.

As the microCT imaging establishes, a successful regional composite was fabricated having surface material localized to surface regions of a core material. In this example, the regional composite structure will allow the PEEK core material to provide structural support while the bioactive glass layer can stimulate formation of a strong implant-tissue interface. This particular combination of materials is preferred due to the inherent bone bonding properties of bioactive glass and its resorbability. These materials improve tissue bonding through the bioactive properties of the glass and then create a porous tissue ingrowth layer once the bioactive glass is resorbed.

Both 45S5 and S53P4 glasses are preferred bioactive glasses and are known to be bioactive which results in the direct apposition of a bone mineral layer on its surface and a strong bond between glass and bone. As the material is resorbed, it is replaced by bone. In a PEEK/bioactive glass implant, initial bone bonding occurs through a chemical process due to the bioactivity of the glass. The interface then transitions to an equally strong mechanical interlock as bone grows into the spaces previously occupied by the bioactive glass spheres.

This type of healing is highly advantages to spinal fusion applications where an implant would bond to the vertebral endplates or in sports medicine applications where implant pull-out strength is critical.

What is claimed is:

1. A composite composition comprising:
   (a) a core material and (b) a surface material,
      wherein the core material comprises a surface region,
      wherein the surface region comprise(s), throughout the entire surface region, a layer of the surface material,
      wherein the layer of the surface material has a substantially uniform thickness throughout the surface region and,
      wherein the surface region comprises about 20% to about 99% by weight of the surface material, wherein the x, y, and z cross-sections of the composite composition does not exhibit substantial material uniformity.

2. The composite composition of claim 1, wherein the core material comprises polyetheretherketone (PEEK), polyetherketoneketone (PEKK), polyaryletherketone (PAEK), polyurethanes, polyethylene, polypropylene, polyamides, polyarylamides, polymethylmethacrylate (PMMA), polytetrafluoroethylene, titanium, titanium alloys, stainless steel, tantalum, silicon nitride, poly (hydroxy acids), polyanhydrides, polycaprolactone, or a combination thereof.

3. The composite composition of claim 1, wherein the surface material is resorbable.

4. The composite composition of claim 1, wherein the surface material is non-resorbable.

5. The composite composition of claim 1, wherein the surface material is a combination of a resorbable material and a non-resorbable material.

6. The composite composition of claim 3, wherein the core material is resorbable, and the resorption rate of the core material and the resorption rate of the surface material are different.

7. The composite composition of claim 1, wherein the core material is non-resorbable.

8. The composite composition of claim 1, wherein the core material is a composite material comprising two or more materials.

9. The composite composition of claim 1, wherein the surface material comprises bioactive glass, hydroxyapatite (HA), tricalcium phosphate (TCP), biphasic calcium phosphate (HA-TCP), tetracalcium phosphate, brushite, fluorapatite, calcium pyrophosphate, calcium sulfate, titanium, titanium alloys, stainless steel, tantalum, silicon nitride, zirconium, niobium, or a combination thereof.

10. The composite composition of claim 1, wherein the surface material is embedded in the core material.

11. The composite composition of claim 1, wherein a portion of the surface material is partially embedded in the core material.

12. The composite composition of claim 1, wherein the layer of surface material has a substantially uniform thickness of about 0.5 mm to about 10 mm throughout the surface region.

13. The composite composition of claim 12, wherein the thickness of the layer of the surface material is about 0.5 mm to about 5 mm throughout the surface region.

14. The composite composition of claim 1, wherein the surface material comprises a porous surface material.

15. The composite composition of claim 14, further comprising a therapeutic agent absorbed or adsorbed to the open pores of the porous surface material.

16. The composite composition of claim 1, wherein the surface material is in the form of a particle, granule, fiber, or 3-dimensional geometric shape.

17. The composite composition of claim 16, wherein the fiber surface material is in the form of a woven fiber structure, non-woven fiber structure, segmented fiber structure, or continuous fiber structure.

18. The composite composition of claim 1, wherein the surface material comprises bioactive glass spheres.

19. The composite composition of claim 18, wherein the bioactive glass spheres comprise 45S5 glass or S53P4 glass.

20. The composite composition of claim 18, wherein the bioactive glass spheres have a particle size of about 32 microns to about 800 microns.

21. The composite composition of claim 18, wherein the bioactive glass spheres have a bimodal particle size distribution.

22. The composite composition of claim 1, wherein the surface material comprises titanium.

23. The composite composition of claim 22, wherein the core material comprises polyetheretherketone (PEEK).

24. The composite composition of claim 23, wherein the surface material is in the form of a particle, granule, fiber, or 3-dimensional geometric shape.

25. The composite composition of claim 24, wherein the fiber surface material is in the form of a woven fiber structure, non-woven fiber structure, segmented fiber structure, or continuous fiber structure.

26. A shaped structure comprising the composite composition of claim 1.

27. The shaped structure of claim 26, in the form of a surgical implant, an interbody spacer, a suture anchor, a surgical screw, a surgical plate, or an anterior cruciate ligament (ACL) interference screw.

28. The shaped structure of claim 26, wherein when the shaped structure is implanted in a mammalian body the surface region is in contact with tissue that is to be attached to the shaped structure.

29. The shaped structure of claim 28, wherein the tissue to be attached is bone.

30. A method of making the shaped structure claim 27, comprising one of:
   heating a core material to a semi-molten state and pressing the surface material into one or more surface regions of the semi-molten core material;
   melting a core material and pouring the melted core material over a layer of a surface material;
   compression-molding at least one layer of surface material on one or more surface regions of a layer of a core material;
   melt processing a layer of surface material, machining the melt-processed layer of surface material into a predetermined shape, and sintering or melting the machined shape of surface material onto one or more surface regions of the core material; or
   3-D printing or laser sintering a layer of a core material, and 3-D printing or laser sintering a layer of surface material on one or more surface regions of the core material;
   or a combination thereof.

31. The method of claim 30, further comprising a surface removal step.

32. The method of claim 31, wherein the surface removal step comprises machining the shaped structure, particle blasting the shaped structure, and/or sanding the shaped structure.

33. A shaped structure according to claim 27 formed by the method of claim 30.

34. The composite composition of claim 12, wherein the thickness of the layer of the surface material is about 2 mm throughout the surface region.

35. A method of promoting healing, comprising implanting into a mammalian subject the shaped structure of claim 26, wherein the surface region of the shaped structure is in contact with tissue that is to be attached.

36. The method of claim 35, wherein the tissue that is to be attached is bone.

* * * * *